US009603888B2

(12) United States Patent
Georgi et al.

(10) Patent No.: US 9,603,888 B2
(45) Date of Patent: Mar. 28, 2017

(54) PEA PROTEIN PEPTIDES WITH ANTI HELICOBACTER PYLORI ACTIVITY

(71) Applicant: N.V. Nutricia, Zoetermeer (NL)

(72) Inventors: Gilda Elise Georgi, Hösbach (DE); Marco Euler, Wölfersheim (DE); Marko Mank, Allendorf (DE); Andreas Hensel, Münster (DE); Michael Niehues, Münster (DE); Monika Klapperich, Usingen (DE); Bernd Stahl, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 14/637,057

(22) Filed: Mar. 3, 2015

(65) Prior Publication Data

US 2015/0174192 A1 Jun. 25, 2015

Related U.S. Application Data

(62) Division of application No. 13/637,881, filed as application No. PCT/NL2011/050211 on Mar. 29, 2011, now Pat. No. 8,999,924.

(30) Foreign Application Priority Data

Mar. 29, 2010 (WO) ................ PCT/NL2010/050158

(51) Int. Cl.
*A61K 38/01* (2006.01)
*A23L 1/305* (2006.01)
*A61K 38/08* (2006.01)
*A61K 38/10* (2006.01)
*C07K 14/415* (2006.01)
*C07K 7/06* (2006.01)
*C07K 7/08* (2006.01)

(52) U.S. Cl.
CPC ............ *A61K 38/011* (2013.01); *A23L 33/17* (2016.08); *A23L 33/175* (2016.08); *A23L 33/18* (2016.08); *A23L 33/185* (2016.08); *A23L 33/19* (2016.08); *A61K 38/08* (2013.01); *A61K 38/10* (2013.01); *C07K 7/06* (2013.01); *C07K 7/08* (2013.01); *C07K 14/415* (2013.01); *A23V 2002/00* (2013.01)

(58) Field of Classification Search
None
See application file for complete search history.

(56) References Cited

FOREIGN PATENT DOCUMENTS

| DE | 103 17 935 A1 | 11/2004 |
|----|---------------|---------|
| EP | 1-178 104 A1 | 2/2002 |
| EP | 1 911 457 A1 | 4/2008 |
| JP | 2001-335504 | 12/2001 |
| JP | 2005-255679 | 9/2005 |
| WO | WO-02/071863 A1 | 9/2002 |
| WO | WO-2008/043424 | 4/2008 |

OTHER PUBLICATIONS (http://www.biology-online.org/dictionary/Pathogens, accessed May 9, 2013).
Bucinski et al. (Modeling the tryptic hydrolysis of pea proteins using an artificial neural network, The Swiss Society of food science and technology (2008), pp. 942-945).
Frqczek et al. (Immunogenic potential of antigens isolated from trypsin Pea protein hydrolysates, Polish Journal of Good and Nutrition Sciences (2008), vol. 58 No. 4, pp. 491-496).
Gastrointestinal Tract Infections, p. 253-286, created Mar. 22, 2001. http://animaldiversity.ummz.umich.edu/accounts/Mammalia/, accessed Dec. 12, 2013.
International Preliminary Report on Patentability for PCT/NL2011/050211—mailed Feb. 22, 2012.
International Search Report for PCT/NL2011/050211—mailed May 11, 2011.
Roussere et al. (Emerging Infectious Diseases, vol. 9 (12), 2003.
Soral-Smietana et al. (Nahrung 42 (1998) p. 217-218).

*Primary Examiner* — James H Alstrum Acevedo
*Assistant Examiner* — Tara Martinez
(74) *Attorney, Agent, or Firm* — Foley & Lardner LLP; Sunit Talapatra

(57) ABSTRACT

The invention relates to a composition comprising pea protein hydrolysate for the treatment and/or prevention of infection by gastrointestinal pathogens, in particular *Helicobacter pylori* and/or a disease associated with infection by said gastrointestinal pathogen in mammals.

8 Claims, No Drawings

PEA PROTEIN PEPTIDES WITH ANTI HELICOBACTER PYLORI ACTIVITY

CROSS-REFERENCE TO RELATED APPLICATIONS

This application is a divisional of U.S. patent application Ser. No. 13/637,881, filed Jan. 11, 2013, which was filed as the National Phase of International Patent Application No. PCT/NL2011/050211, filed Mar. 29, 2011, published as WO 2011/122944, which claims priority to International Application No. PCT/NL2010/050158, filed Mar. 29, 2010. The contents of these applications are herein incorporated by reference in their entirety.

SEQUENCE LISTING

The instant application contains a Sequence Listing which has been submitted in ASCII format via EFS-Web and is hereby incorporated by reference in its entirety. Said ASCII copy, created on Apr. 22, 2013, is named 069818-7275_SL.txt and is 5,273 bytes in size.

FIELD OF THE INVENTION

The present invention relates to the treatment and/or prevention of infection by gastrointestinal pathogens, in particular *Helicobacter pylori*.

BACKGROUND OF THE INVENTION

Gastrointestinal infections are a major problem in many humans, and particularly in infant and patients with an impaired immune system or gastrointestinal diseases. The resulting diseases can be life threatening. Gastrointestinal infections are often caused by *Escherichia coli, Salmonella, Campylobacter, Porphyromonas gingivalis, Clostridium, Enterobacter* and *Helicobacter*, e.g. *Helicobacter pylori*.

*Helicobacter pylori* (*H. pylori*) is a Gram-negative, microaerophilic flagellated bacterium that colonizes the gastric mucosa of humans upon infection. *H. pylori* infection has been associated with severe gastric diseases, such as gastritis, peptic ulcer and gastric cancer. *H. pylori* has been classified as a Group I carcinogen by the World Health Organisation. *H. pylori* infection is usually chronic and mostly not heals without specific therapy.

*H. pylori* infection is mainly acquired in early childhood. Most children are infected during the first 5 years of life. By the age of 10, overall prevalence is more than 75% in developing countries, whereas 10% are infected in developed countries, but prevalence can rise to 30-40% in children from lower socio-economic groups.

With regard to problems of treatment by antibiotics and prophylaxis by vaccination the adhesion, and therefore the infection of *H. pylori* to the gastric mucosa should be prevented, ideally by dietary oral intervention.

Treatment to eradicate *H. pylori* infection requires three to four medications with antibiotics. Treatment is very expensive and there is also the risk of increasing antibiotic resistance in bacterial strains and re-infection following unsuccessful therapy. Treatment of children may be the most cost effective method of reducing the incidence of infection and the morbidity and mortality associated with *H. pylori* related diseases. So far there are no guidelines on the need to treat children. A human vaccine is not yet available. Prophylaxis and therapeutic vaccination have been successful in animal models, but the translation to a human vaccine remains difficult, in part because the immunology of the stomach is still poorly understood.

With regard to the problems of treatment by antibiotics and prophylaxis by vaccination, the adhesion of *H. pylori* to the gastric mucosa should be prevented. Without adhesion of the bacteria, the risk of a related inflammation resulting in gastritis or possibly in cancer can be minimised. Dietary modulation has proven to be useful in supporting *H. pylori* infection treatment or prophylaxis in vivo and in vitro EP 1178104 relates to a nutritional composition comprising a specific essential oil and/or specific pure compound isolated from the essential oil for prevention or treatment of infection by a *Helicobacter*-like organism. The nutritional composition may also contain a source of carbohydrates, a source of fat and/or a source of a dietary protein, pea protein being one of them.

JP 2005255679 describes a polypeptide obtained by treating butter milk with a protease having not only adhesion inhibitory effect of *Helicobacter pylori* to gastric mucosa but also the effect of debonding *Helicobacter pylori* off the gastric mucosa of *Helicobacter pylori* carriers.

JP 2001335504 describes a proliferation inhibitor of *Helicobacter pylori* that comprises a soybean protein enzymic hydrolysate as an active ingredient.

WO 2008/043424 discloses a composition for the treatment and/or prevention of infection by gastrointestinal pathogens, in particular *Helicobacter pylori* and/or a disease associated with infection by said gastrointestinal pathogen in mammals. The composition comprises a pea protein hydrolysate, intact pea protein and/or camel milk protein hydrolysate. A pea protein hydrolysate obtained by hydrolysis by chymotrypsin and trypsin is disclosed.

DE 10317935 describes the use of casein to prepare a composition for prevention or treatment of *Helicobacter* infection and for preventing diseases caused by *Helicobacter* infection.

SUMMARY OF THE INVENTION

The present invention relates to the use of a composition comprising specific pea protein peptides for the treatment and/or prevention of infection by gastrointestinal pathogens and/or a disease associated with infection by said gastrointestinal pathogen in mammals, particularly infections by gastrointestinal pathogen selected from the group consisting of *Helicobacter, Escherichia coli, Salmonella, Porphyromonos gingivalis, Campylobacter, Clostridium* and *Enterobacter*. The invention relates furthermore to the use of specific pea protein hydrolysate, not produced by chymotrypsin hydrolysis, for the preparation of a composition for the treatment and/or prevention of the infection or disease, specified above.

The present inventors have found that a specific pea protein hydrolysate is able to inhibit the adhesion of *H. pylori* to gastric mucosa cells. The inhibition of adhesion makes these protein components particularly suitable for the use in a method for the treatment and/or prevention of *Helicobacter* infection. The pea protein hydrolysate has been obtained by hydrolysis of pea protein isolate by trypsin. The peptides responsible for inhibition of adhesion were isolated and identified. The peptides of the present invention Asp-Phe-Leu-Glu-Asp-Ala-Phe-Asn-Val-Asn-Arg (SEQ ID NO:1) and Glu-Leu-Ala-Phe-Pro-Gly-Ser-Ala-Gln-Glu-Val-Asp-Arg (SEQ ID NO:2), forming part of pea legumin A and vicilin, were found to inhibit adhesion of *H. pylori* to gastric cells. Since these peptides have a chymotrypsin cleavage site, the pea protein hydrolysate can be obtained by hydrolysis by proteases, preferably by trypsin, provided the protease is not chymotrypsin, or with a protease preparation, preferably trypsin preparation, that has no substantial chymotrypsin activity.

The present pea protein hydrolysate and/or pea protein peptides can be easily added to infant formulas, toddler products, and products for young people. The easy and safe use of this protein component makes the invention of particular importance, as the problems of side effect normally encountered with medicaments and the costly multi-medicine therapies are circumvented. The present pea protein hydrolysate and/or pea protein peptides can also suitably be used by adults. The present pea protein hydrolysate and/or pea protein peptides do not have to be administered separately (e.g. to infants), but can be co-administered within a nutritional composition.

Because increased duration of exclusive breastfeeding in infancy may have a long-term protective effect against chronic H. pylori infection and hence the risk of gastric carcinoma, it is particularly desirable to also protect infants which receive infant formula against H. pylori infection.

DETAILED DESCRIPTION

The present invention thus concerns a method for the treatment and/or prevention and/or reduction of risk of infection by gastrointestinal pathogens and/or a disease associated with infection by gastrointestinal pathogens in a mammal, said method comprising administering to said mammal a composition comprising pea protein hydrolysate, provided that said pea protein hydrolysate is not obtained by hydrolysis by the protease chymotrypsin. Preferably the pea protein hydrolysate is obtained by hydrolysis with protease other than chymotrypsin.

The invention can also be worded as the use of a composition comprising pea protein hydrolysate for the manufacture of a composition for treatment and/or prevention of infection by gastrointestinal pathogens and/or a disease associated with infection by gastrointestinal pathogens in a mammal, provided that said pea protein hydrolysate is not obtained by hydrolysis by the protease chymotrypsin.

The invention can also be worded as a composition comprising pea protein hydrolysate for use in the treatment and/or prevention of infection by gastrointestinal pathogens and/or a disease associated with infection by gastrointestinal pathogens in a mammal, provided that said pea protein hydrolysate is not obtained by hydrolysis by the protease chymotrypsin.

In one aspect the invention concerns a method for the treatment and/or prevention and/or reduction of risk of infection by gastrointestinal pathogens and/or a disease associated with infection by gastrointestinal pathogens in a mammal, said method comprising administering to said mammal a composition comprising at least one peptide selected from the group consisting of $Xaa_n$-Asp-Phe-Leu-Glu-Asp-Ala-Phe-Asn-Val-Asn-Arg-$Xaa_m$ (SEQ ID NO: 14) and $Xaa_n$-Glu-Leu-Ala-Phe-Pro-Gly-Ser-Ala-Gln-Glu-Val-Asp-Arg-$Xaa_m$ (SEQ ID NO: 15), wherein each Xaa independently can be any amino acid and n and m are integers independently ranging from 0-10.

The invention can also be worded as the use of a composition comprising peptide for the manufacture of a composition for treatment and/or prevention of infection by gastrointestinal pathogens and/or a disease associated with infection by gastrointestinal pathogens in a mammal, wherein the peptide is selected from the group consisting of $Xaa_n$-Asp-Phe-Leu-Glu-Asp-Ala-Phe-Asn-Val-Asn-Arg-$Xaa_m$ (SEQ ID NO: 14) and $Xaa_n$-Glu-Leu-Ala-Phe-Pro-Gly-Ser-Ala-Gln-Glu-Val-Asp-Arg-$Xaa_m$ (SEQ ID NO: 15), wherein each Xaa independently can be any amino acid and n and m are integers independently ranging from 0-10.

The invention can also be worded as a composition comprising at least one peptide selected from the group consisting of $Xaa_n$-Asp-Phe-Leu-Glu-Asp-Ala-Phe-Asn-Val-Asn-Arg-$Xaa_m$ (SEQ ID NO: 14) and $Xaa_n$-Glu-Leu-Ala-Phe-Pro-Gly-Ser-Ala-Gln-Glu-Val-Asp-Arg-$Xaa_m$ (SEQ ID NO: 15), wherein each Xaa independently can be any amino acid and n and m are integers independently ranging from 0-10 for use in the treatment and/or prevention of infection by gastrointestinal pathogens and/or a disease associated with infection by gastrointestinal pathogens in a mammal.

In a further aspect, the invention also concerns a composition containing a lipid, protein and carbohydrate constituent wherein the lipid constituent provides 5 to 50% of the total calories, the protein constituent provides 5 to 50% of the total calories and the carbohydrate constituent provides 15 to 90% of the total calories, wherein the protein constituent comprises (i) at least one protein source consisting of pea protein hydrolysate, provided that the pea protein hydrolysate is not obtained by hydrolysis by the protease chymotrypsin and (ii) at least one nitrogen source selected from the group consisting of milk proteins, milk protein hydrolysate, egg proteins, egg protein hydrolysate, soy protein, soy protein hydrolysate, wheat protein, wheat protein hydrolysate, rice protein, rice protein hydrolysate, free amino acids and mixtures thereof.

In yet another aspect, the invention concerns a composition containing a lipid, protein and carbohydrate constituent wherein the lipid constituent provides 5 to 50% of the total calories, the protein constituent provides 5 to 50% of the total calories and the carbohydrate constituent provides 15 to 90% of the total calories, wherein the protein constituent comprises (i) at least one peptide selected from the group consisting of $Xaa_n$-Asp-Phe-Leu-Glu-Asp-Ala-Phe-Asn-Val-Asn-Arg-$Xaa_m$ (SEQ ID NO: 14) and $Xaa_n$-Glu-Leu-Ala-Phe-Pro-Gly-Ser-Ala-Gln-Glu-Val-Asp-Arg-$Xaa_m$ (SEQ ID NO: 15), wherein each Xaa independently can be any amino acid and n and m are integers independently ranging from 0-10 and (ii) at least one nitrogen source selected from the group consisting of milk proteins, milk protein hydrolysate, egg proteins, egg protein hydrolysate, soy protein, soy protein hydrolysate, wheat protein, wheat protein hydrolysate, rice protein, rice protein hydrolysate, free amino acids and mixtures thereof.

Protein

The present invention provides a composition, and the use thereof for the present treatments, containing a pea protein hydrolysate, obtained by proteases other than chymotrypsin. Preferably the pea protein hydrolysate is obtained by hydrolysis with protease other than chymotrypsin, more preferably the pea protein hydrolysate is obtained by hydrolysis with trypsin. More preferably the present invention provides specific pea protein degradation peptides obtainable trypsin hydolysis, namely $Xaa_n$-Asp-Phe-Leu-Glu-Asp-Ala-Phe-Asn-Val-Asn-Arg-$Xaa_m$ (SEQ ID NO: 14) and $Xaa_n$-Glu-Leu-Ala-Phe-Pro-Gly-Ser-Ala-Gln-Glu-Val-Asp-Arg-$Xaa_m$ (SEQ ID NO: 15), wherein each Xaa independently can be any amino acid and n and m are integers independently ranging from 0-10. Hence n and m independently may be 0, 1, 2, 3, 4, 5, 6, 7, 8, 9 or 10. In a preferred embodiment, each of the peptides $Xaa_n$-Asp-Phe-Leu-Glu-Asp-Ala-Phe-Asn-Val-Asn-Arg-$Xaa_m$ (SEQ ID NO: 14) and $Xaa_n$-Glu-Leu-Ala-Phe-Pro-Gly-Ser-Ala-Gln-Glu-Val-Asp-Arg-$Xaa_m$ (SEQ ID NO: 15) has a calculated molecular weight between 1 kDa and 2.5 kDa, preferably between 1 kDa and 2 kDa, preferably between 1 and 1.5 kDa. In one embodiment n and m are 0. Since these peptides have a chymotrypsin cleavage site, and since smaller fragments of these peptides were found to be inactive, the pea protein hydrolysate cannot be obtained by hydrolysis with chymotrypsin or with trypsin plus chymotrypsin. Upon consuming these peptides, they will be further degraded in the human intestinal tract. However, since chymotrypsin and other enzymes as carboxy and amino peptidases are released only in the duodenum, the peptides are still present in their active form in the stomach, the site where *H. pylori* is mainly present. Since these peptides were also found to be derived from the pea protein legumin A or vicilin, the pea protein hydrolysate is preferably a pea legumin A and/or pea vicilin hydrolysate obtained by proteases other than chymotrypsin, preferably by trypsin. Commercial preparations of proteases other than chymotrypsin may contain minor contaminations of chymotrypsin and thus may exhibit some chymotrypsin activity. This is acceptable for preparing the present hydrolysates. Minor chymotrypsin activity will not lead to substantial hydrolysis within the peptides of SEQ ID NO:1 and SEQ ID NO:2. Some residual chymotrypsin activity in protease preparations, in particular trypsin preparations, is considered only to be of influence for the yield of peptides in the hydrolysate comprising the sequence of SEQ ID NO:1 or SEQ ID NO:2. Methods to hydrolyse pea protein are known in the art. Thus preferably the peptides of SEQ ID NO:1 and SEQ ID NO:2 originate from pea protein, it may however also be provided by a different source. Thus in on embodiment the peptides of SEQ ID NO:1 and/or SEQ ID NO:2 are provided in the form of a food grade protein. In one embodiment the peptides of SEQ ID NO:1 and/or SEQ ID NO:2 are provided in the form of pea protein hydrolysate.

By gel filtration chromatography, a chromatographic methodology based on cross-linked agarose/dextran matrix, the molecular weight range of the most effective anti-*helicobacter* adhesive peptides and/or glycoconjugates in the present protein hydrolysate was determined. It was found that effective anti-*helicobacter* adhesive peptides lie within the range 300-10000 Da. Preferably effective anti-*helicobacter* adhesive peptides lie within the range 500-5000 Da. Hence the present protein hydrolysate preferably contains at least 1 wt. % peptides and/or glycoconjugates, preferably peptides, based on total weight of the present protein hydrolysate, with a molecular weight of 300 to 10000 Da, preferably at least 5 wt. %, more preferably at least 50 wt. %, most preferably at least 75 wt. %. More preferably the present protein hydrolysate comprises at least 1 wt. % peptides and/or glycoconjugates, preferably peptides, based on total weight of the present protein hydrolysate, with a molecular weight of 500 to 5000 Da, preferably at least 5 wt. %, more preferably at least 50 wt. %, most preferably at least 75 wt. %. Unless stated otherwise, the molecular weights mentioned herein are determined by gel filtration chromatography.

The present pea protein hydrolysate is preferably administered in an amount of 0.1 to 100 grams per day, preferably in an amount of 0.5 to 10 grams per day. The present pea protein peptides can be administered in a lower dose, namely in an amount of 0.005 to 50 grams per day, preferably in an amount of 0.05 to 5 grams per day.

Most preferably the pea peptides of the present invention are administered in the form of a pea protein hydrolysate. Alternatively, the pea peptides of the present invention may be synthesized or expressed via genetically modified (micro-)organisms.

Preferably the composition comprises pea protein hydrolysate, more preferably a fraction pea protein hydrolysate of less than 10 kDa, more preferably of less than 7.5 kDa, since the administration of the hydrolysate were the most active in preventing *H. pylori* adhesion. A preferred pea protein hydrolysate fraction has an average molecular weight of around 2 kDa. A preferred pea protein hydrolysate fraction has a high concentration in the 1 kDa to 2.5 kDa range. Therefore preferably pea peptides are used, obtained by trypsin hydrolysis, with a size of between 1 and 2.5 kDa. Preferably the pea protein hydrolysate comprises over 35 wt. %, more preferably over 40 wt. % peptides with a size of 1 kDa to 2.5 kDa, based on total weight of the pea protein hydrolysate.

Gastrointestinal Pathogens

The present method relates to the treatment and/or prevention of infection by gastrointestinal pathogens and/or a disease associated with infection by said gastrointestinal pathogen in mammals, particularly the treatment and/or prevention of infections by a gastrointestinal pathogen which is selected from the group consisting of *Helicobacter, Escherichia coli, Salmonella, Porphyromonas gingivalis, Campylobacter, Clostridium* and *Enterobacter* and/or a disease associated with infection by said gastrointestinal pathogen in mammals.

The present invention particularly provides for the treatment and/or prevention of infections by *Helicobacter* and/or a disease associated with infection by *Helicobacter* in mammals. The *Helicobacter* is preferably selected from the group consisting of *Helicobacter pylori, Helicobacter bizzozeronii, H. salomonis, Helicobacter heilmannii* and *Helicobacter felis*. Preferably the present invention provides the treatment and/or prevention of infections by *Helicobacter pylori* (*H. pylori*) and/or a disease associated with infection by *Helicobacter pylori* in mammals.

Food Compositions

It was found that the present pea protein hydrolysate and/or pea protein peptides can be advantageously applied in food, such as baby food and clinical nutrition, particularly infant nutrition. The present nutritional composition preferably comprises a lipid constituent, a protein constituent and carbohydrate constituent.

Hence, the present invention also relates to a nutritional composition comprising the present pea protein hydrolysate and/or pea protein peptides and the use thereof in the present method, wherein the lipid constituent provides 5 to 50% of the total calories, the protein constituent provides 5 to 50% of the total calories, the carbohydrate constituent provides 15 to 90% of the total calories. The present composition is preferably used as an infant formula, wherein the lipid constituent provides 35 to 50% of the total calories, the protein constituent provides 7.5 to 12.5% of the total calories, and the carbohydrate constituent provides 40 to 55% of the total calories. For calculation of the % of total calories for the protein constituent, the total of proteins, peptides and amino acids needs to be taken.

Besides the present pea protein hydrolysate and/or pea protein peptides the present composition preferably contains an additional nitrogen source for nutritional purposes. The additional nitrogen source is preferably selected from the group consisting of protein, peptide, amino acids and mixtures thereof. Hence, in a preferred embodiment the protein component of the present composition comprises: (i) at least one protein source selected from pea protein hydrolysate not obtained by chymotrypsin hydrolysis, and/or pea protein peptides; and (ii) at least nitrogen source selected from the group consisting of milk proteins, egg proteins, soy protein, wheat protein, rice protein, free amino acids and mixtures thereof. Preferably the present composition comprises (i) pea protein hydrolysate not obtained by chymotrypsin hydrolysis and/or pea protein peptides and (ii) at least one nitrogen source selected from the group of hydrolysed cow's whey, non-hydrolysed cow's whey, hydrolysed cow's casein, non hydrolysed cow's casein and non-hydrolysed soy protein. Preferably the pea protein hydrolysate is obtained by trypsin hydrolysis.

When the present protein component and in particular the present pea protein hydrolysate and/or pea protein peptides is administered in combination with an additional nitrogen source, the present composition preferably comprises between 0.1 and 50 wt. % of the present pea protein hydrolysate and/or pea protein peptides and in particular between 1 and 10 wt. % of the present pea protein hydrolysate and/or pea protein peptides based on total weight of protein.

When the present protein component and in particular the present pea protein hydrolysate is administered in combination with an additional nitrogen source, the present composition preferably comprises between 1 and 50 wt. % of the present pea protein hydrolysate and/or pea protein peptides and in particular between 1 and 10 wt. % of the present pea protein hydrolysate based on total weight of protein.

When the present protein component and in particular the present pea protein peptides is administered in combination with an additional nitrogen source, the present composition preferably comprises between 0.1 and 50 wt. % of the present pea protein hydrolysate and/or pea protein peptides and in particular between 0.1 and 10 wt. % of the present pea protein hydrolysate and/or pea protein peptides based on total weight of protein.

A source of digestible carbohydrate may be added to the nutritional formula. The present composition preferably contains lactose.

In a preferred embodiment the anti-infective effect against the gastrointestinal pathogen of the present protein component and in particular the present pea protein hydrolysate and/or pea protein peptides, is improved by co-administration of a soluble, non-digestible, fermentable oligosaccharide. Administration of these oligosaccharides stimulates the growth of lactic acid bacteria such as bifidobacteria and lactobacilli, preventing colonization and infection by gastrointestinal pathogens. Hence the present pea protein hydrolysate and/or pea protein peptides and present oligosaccharide act synergistically in this respect.

Preferably the present composition comprises non-digestible oligosaccharides with a degree of polymerization (DP) between 2 and 250, more preferably 3 and 60. The non-digestible oligosaccharide is preferably selected from the group consisting of fructo-oligosaccharides (such as inulin), galacto-oligosaccharides (such as transgalacto-oligosaccharides or beta-galacto-oligosaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. Preferably the composition comprises gum acacia on combination with a non-digestible oligosaccharide.

Preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of transgalacto-oligosaccharides and fructo-oligosaccharides. Preferably the present composition comprises galacto-oligosaccharides with a DP of 2-10 and/or fructo-oligosaccharides with a DP of 2-60. The galacto-oligosaccharide is preferably selected from the group consisting of transgalacto-oligosaccharides, lacto-N-tetraose (LNT), lacto-N-neotetraose (neo-LNT), fucosyl-lactose, fucosylated LNT and fucosylated neo-LNT. In a particularly preferred embodiment the present method comprises the administration of transgalacto-oligosaccharides ([galactose]$_n$-glucose; wherein n is an integer between 1 and 60, i.e. 2, 3, 4, 5, 6, ..., 59, 60; preferably n is selected from 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are β-linked.

Fructo-oligosaccharide is a non-digestible oligosaccharide comprising a chain of β linked fructose units with a DP or average DP of 2 to 250, more preferably 10 to 100. Fructo-oligosaccharide includes inulin, levan and/or a mixed type of polyfructan. An especially preferred fructo-oligosaccharide is inulin. Fructo-oligosaccharide suitable for use in the compositions is also already commercially available, e.g. Raftiline®HP (Orafti).

Uronic acid oligosaccharides are preferably obtained from pectin degradation. Uronic acid oligosaccharides are preferably galacturonic acid oligosaccharides. Hence the present composition preferably comprises a pectin degradation product with a DP between 2 and 100. Preferably the pectin degradation product is prepared from apple pectin, beet pectin and/or citrus pectin. Preferably the composition comprises transgalacto-oligosaccharide, fructo-oligosaccharide and a pectin degradation product. The weight ratio transgalacto-oligosaccharide:fructo-oligosaccharide:pectin degradation product is preferably (20 to 2):1:(1 to 3), more preferably (12 to 7):1:(1 to 2).

Preferably, the uronic acid oligosaccharide has one, preferably two, terminal uronic acid units, which may be free or esterified. Preferably the terminal uronic acid unit is selected from the group consisting of galacturonic acid, glucuronic acid, guluronic acid, iduronic acid, mannuronic acid, riburonic acid and altruronic acid. These units may be free or esterified. In an even more preferred embodiment, the terminal hexose unit (i.e. uronic acid) has a double bond, which is preferably situated between the C4 and C5 position of the terminal hexose unit. Preferably one of the terminal hexose units comprises the double bond. The carboxylic acid groups on these uronic acid units may be free or (partly) esterified, and are preferably at least partly methylated.

The uronic acid oligosaccharides used in the invention are preferably prepared from pectin, pectate, alginate, chondroitine, hyaluronic acids, heparine, heparane, bacterial carbohydrates, sialoglycans, fucoidan, fucooligosaccharides or carrageenan, more preferably from pectin and/or alginate. The uronic acid oligosaccharides are preferably prepared by enzymatic digestion with lysase, lyase and/or endopolygalacturonase. Preferably pectin hydrolysate or lysate is used. The present uronic acid oligosaccharide is preferably obtainable by enzymatic digestion of pectin with pectin lysase, pectic lyase, endopolygalacturonase and/or pectinase.

Such uronic acid oligosaccharides prevent adhesion of intestinal pathogens. Compositions comprising the pea protein peptides/hydrolysate of the present invention and the uronic acid oligosaccharide will have an improved anti-*H. pylori* effect.

A preferred oligosaccharide is sialyllactose, more preferably 3'-sialyllactose, since this oligosaccharide also interferes with *H. pylori* adhesion. Compositions of the present invention additionally comprising sialyllactose, preferably 3' sialyllactose will therefore have an improved anti *H. pylori* effect.

Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. %.

Thus in another embodiment, the present invention concerns a composition comprising a non-digestible oligosaccharide selected from the group consisting of trans-galactooligosaccharide, fructo-oligosaccharides, uronic acid oligosaccharide and sialyllactose and
a) pea protein hydrolysate, provided that said pea protein hydrolysate is not obtained by hydrolysis by the protease chymotrypsinor or preferably pea protein hydrolysate which is obtained by hydrolysis with protease other than chymotrypsin; and/or
b) at least one peptide selected from the group consisting of $Xaa_n$-Asp-Phe-Leu-Glu-Asp-Ala-Phe-Asn-Val-Asn-Arg-$Xaa_m$ (SEQ ID NO: 14) and $Xaa_n$-Glu-Leu-Ala-Phe-Pro-Gly-Ser-Ala-Gln-Glu-Val-Asp-Arg-$Xaa_m$ (SEQ ID NO: 15), wherein each Xaa independently can be any amino acid and n and m are integers independently ranging from 0-10.

Stool irregularities (e.g. hard stools, insufficient stool volume, diarrhea) is a particular problem in many babies and ill subjects that have or are at risk of a *H. pylori* infection. These subjects often receive liquid foods. It was found that stool problems may be reduced by administering the present pea protein hydrolysate component and/or pea protein peptides in liquid foods which have an osmolality between 50 and 500 mOsm/kg, more preferably between 100 and 400 mOsm/kg. The prevention of stool problems is of particular importance when the present pea protein hydrolysate and/or pea protein peptides are used together or after treatment with antibiotics. In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml, most preferably between 0.6 and 0.8 kcal/ml.

Application

The present invention provides a composition for and a method of the treatment and/or prevention of infection by gastrointestinal pathogens (particularly *H. pylori*) and/or a disease associated with infection by gastrointestinal pathogens (particularly *H. pylori*) in a mammal, preferably a human subject, said method comprising administering the present pea protein hydrolysate and/or pea protein peptides to the mammal or human subject. Diseases associated with infection by gastrointestinal pathogens in humans include persistent chronic gastritis, diarrhea, abdominal pain, ulcers and/or stomach cancer. Diseases associated with infection by *H. pylori* in humans include persistent chronic gastritis, ulcers and/or stomach cancer. The present invention also provides for the treatment and/or prevention of these diseases in mammals, preferably human subjects at risk for, or in need for treatment thereof.

The present invention relates to the treatment and/prevention in a mammal, preferably a human or a companion animal, more preferably humans. The present composition is advantageously administered to a) infants with the age between 0 and 5 years, preferably infants between 0 and 2 years and/or b) patients suffering from gastroduodenal diseases, particularly patients suffering from peptic ulcer.

The present invention is also particularly suitable for preventing re-infection with gastrointestinal pathogens, particularly *H. pylori*, after treatment of the mammal with one or more antibiotics.

Example 1

Pea Protein Hydrolysate Fractions Inhibits *H. pylori* Adhesion to Gastric Mucosa 1.1: Anti-Adhesion Assay

*Helicobacter pylori* ATCC 700824 (J99) was cultivated for two or three passages to minimize the risk of phase-variable switching of OMP genes. *H. pylori* was incubated for 48 h under microaerophilic conditions at 37° C. on Tryptic Soy Agar (Becton Dickinson, Germany), supplemented with 5% defibrinated sheep blood (Oxoid, UK).

Human gastric epithelial cells (AGS cells) were grown in RPMI 1640 with L-glutamine (PAA, Germany), supplemented with 10% FCS, on tissue culture flasks (75 cm$^2$, Sarstedt, USA) and 6-well-plates (Sarstedt, USA) in 5% $CO_2$.

Agar grown *H. pylori* were harvested and resuspended in sterile carbonate buffer (pH 9.0) to a density of about $1.0 \times 10^8$ bacteria per ml. 10 µl of a FITC solution (1% in DMSO) were added and incubated with the bacteria for 45 min. Fluorescent labelling was terminated by pelleting the bacteria (3.150×g, 5 min). Bacteria were washed twice in PBS to remove excess FITC and were gently resuspended for further use.

In vitro testing on anti-adhesive activity of test compounds against FITC-labelled *H. pylori* on AGS cells was accomplished by a flow cytometric method (Niehues & Hensel, 2009 J. Pharm. Pharamcol. 61: 1303-1307).

1.2 Bio-Assay Guided Fractionation of the Pea Protein Hydrolysate.

50 Gram of pea protein isolate (Nutralys® F85F, 84% w/w protein from Roquette Frères (Lestrem, France) was dissolved in 1.5 l of distilled water at 50° C. Hydrolysis was started by adding 0.56 g of trypsin (Novo PTN 6.0S, Novozymes A/S, Bagsvaerd, Denmark). The pH was controlled at 7.0 by addition of NaOH. The reaction was allowed to continue for 2 h. The process was stopped by heat inactivation of the enzyme at 85° C. for 5 min. Precipitated material was pelleted by centrifugation at 3,800×g for 20 min at 20° C. and the supernatant ultrafiltered with a plate-and-frame device using a 700 cm$^2$ 10 kDa NMWCO PES membrane (UltranLab, Schleicher & Schuell, Dassel, Germany). The retentate was lyophilized and used for further separation of the pea peptides.

The activity against *H. pylori* was determined as described under 1.1. Pea protein in itself did not exhibit any antiadhesive activity against *H. pylori*. After ultrafiltration of the pea protein hydrolysate antiadhesive activity (56% bacterial adhesion with 0.5 mg/ml) was found within the retentate fraction and not in the permeate fraction.

The 10 kDa retentate was fractionated by size exclusion chromatography (SEC) using a 42×5.0 cm ID column packed with Toyopearl® HW-50S (Tosoh Bioscience GmbH, Stuttgart, Germany). Ammonium hydrogen carbonate 0.1 M, containing 2% (v/v) 2-propanol, was used as mobile phase. The column was operated at a flow rate of 4 ml/min at 4° C. Eluting compounds were monitored at UV 220 nm, fractions collected in 7 ml intervals and pooled to yield four major fractions, namely F1 to F4. F1 being elution volume about 0 to 220 ml and showing an adhesion of 76% at 0.5 mg/ml, F2 being elution volume about 220 to 310 ml and showing an adhesion activity of 94% at 0.5 mg/ml, F3 being elution volume of about 310 to 500 ml and showing an adhesion activity of 25% at 0.5 mg/ml, and F4 being elution volume about 500 to 720 ml and showing an adhesion activity of 118% at 0.5 mg/ml Further purification of F3 was achieved by reversed-phase chromatography (RPC) using a 11.8×1.0 cm ID column packed with Amberchrom® CG-161S resin (Tosoh Bioscience GmbH, Stuttgart, Germany). Mobile phases used were 0.1% (v/v) TFA in distilled water (A) and 0.1% (v/v) TFA in 2-propanol (B). Elution was accomplished with a linear gradient starting from 5% B to 60% B in 7 column volumes, flow rate 0.85 ml/min, UV 220 nm. Fractions of 4 ml each were collected and pooled to obtain three main fractions: F3.1 to F3.3. The fractions were lyophilized before further analysis.

F3.1 having an elution volume of about 3 to 33 ml, showing adhesion activity 109% at 0.5 mg/ml, F3.2 having an elution volume about 33 to 54 ml, showing adhesion activity 112% at 0.5 mg/ml, and F3.3 having an elution volume of about 54 to 85 ml, showing adhesion activity 40% at 0.5 mg/ml, 70% at 0.2 mg/ml, and 78% at 0.1 mg/ml.

The molecular size distribution as determined with Calibration Superdex Peptide 10/300 GL (Amersham Biosciences Cat. No. 17-5176-01). A 2% w/v sample (supernatant after centrifugation) was diluted in 0.1% TFA in 30% ACN/water. Peptides were detected by UV at 214 nm. The size distribution (percentage of total area) was as follows:

| MW Range | GPC F1 (A0622) | GPC F2 (A0623) | GPC F3 (A0624) | GPC F4 (A0625) |
|---|---|---|---|---|
| >10 kDa | 3.7 | 16.4 | 0.0 | 0.0 |
| 10 kDa < > 7.5 kDa | 3.9 | 15.2 | 0.2 | 0.1 |
| 7.5 kDa < > 5 kDa | 11.6 | 16.9 | 1.4 | 0.4 |
| 5 kDa < > 2.5 kDa | 29.0 | 16.3 | 23.9 | 4.3 |
| 2.5 kDa < > 1 kDa | 29.8 | 17.3 | 46.3 | 21.0 |
| 1 kDa < > 0.5 kDa | 11.3 | 9.8 | 16.2 | 23.6 |
| <0.5 kDa | 10.7 | 8.2 | 11.9 | 50.6 |

The average molecular weight of fraction F3 is therefore around 2 kDa with the highest amounts of peptides in the 1 kDa to 2.5 kDa range.

1.3 Identification of the Peptides

For unambiguous identification of active peptides, the fractions F3.1, F3.2 and F3.3 were investigated by MALDI-TOF-TOF tandem MS analysis. Signals of peptides present in the active fractions but not found in the inactive mixtures were specifically selected for subsequent tandem MS-based amino-acid-sequencing. Six peptide sequences (S1 to S6) were determined by this method (Sequences given in Tab. 1) and unambiguously identified with the ProteinPilot™ software suite with the integrated Paragon™ algorithm (Applied Biosystems, Darmstadt, Germany) The following parameters where chosen to enable the amino acid assignment to MALDI-tandem-MS-data by the Paragon™ algorithm: sample type: identification; cystein alkylation: none; digestion: trypsin; instrument: 4800; special factors: none; species: no restriction; ID-focus: biological modifications; database: Uniprot/Swiss-Prot (version Jan. 23, 2007 including a contaminants database, both in the FASTA-format); search effort: thorough.

The peptides S1 to S6 were identified as peptide fragments from pea legumin A or vicilin. Subsequently the respective peptides were synthesized for further unambiguous testing on anti-adhesive properties (Thermo Fisher Scientific (Ulm, Germany). The undecapeptide S3 was found to be the most active compound reducing the bacterial adhesion of *H. pylori* significantly to 81 and 83% respectively (75 resp. 150 µM corresponding to 0.1 resp. 0.2 mg/ml). Also S5, which inhibited adhesion by 6 to 17% (75 resp. 150 µmol), were assessed two of the active peptides obtained from pea protein tryptic digest.

TABLE 1

Sequences of peptides S1 to S6, from synthetic peptides S3A to S3H, with the mean adhesion (±SEM) of FITC-labelled *H. pylori* to AGS cells after pre-treatment of the bacteria with the respective peptides. Data are related to the untreated control of *H. pylori* (=100%). Positive control: 3'sialyllactose (15 mM).

| Test compound | Amino acid sequence | rel. adhesion in [%] (±SEM; n = 3) | |
|---|---|---|---|
| | | 75 µM | 150 µM |
| S1 | Leu-Asp-Ala-Leu-Glu-Pro-Asp-Asn-Arg-Ile-Glu-Ser-Glu-Gly-Gly-Leu-Ile-Glu-Thr-Trp-Asn-Pro-Asn-Asn-Lys (SEQ ID NO: 3) | 95 ± 10 | 104 ± 7 |
| S2 | Leu-Asn-Ile-Gly-Pro-Ser-Ser-Ser-Pro-Asp-Ile-Tyr-Asn-Pro-Glu-Ala-Gly-Arg (SEQ ID NO: 4) | 93 ± 8 | 94 ± 6 |
| S3 | Asp-Phe-Leu-Glu-Asp-Ala-Phe-Asn-Val-Asn-Arg (SEQ ID NO: 1) | 81 ± 3 | 83 ± 6 |
| S4 | Trp-Glu-Arg-Glu-Glu-Asp-Glu-Glu-Gln-Val-Asp-Glu-Glu-Trp-Arg (SEQ ID NO: 5) | 98 ± 2 | 107 ± 2 |
| S5 | Glu-Leu-Ala-Phe-Pro-Gly-Ser-Ala-Gln-Glu-Val-Asp-Arg (SEQ ID NO: 2) | 94 ± 2 | 85 ± 2 |
| S6 | Gly-Asp-Phe-Glu-Leu-Val-Gly-Gln-Arg (SEQ ID NO: 6) | 94 ± 3 | 97 ± 2 |
| S3A | Asp-Phe-Leu-Glu-Asp (SEQ ID NO: 7) | 102 ± 3 | 108 ± 6 |

TABLE 1-continued

Sequences of peptides S1 to S6, from synthetic peptides S3A to S3H, with the mean adhesion (±SEM) of FITC-labelled *H. pylori* to AGS cells after pre-treatment of the bacteria with the respective peptides. Data are related to the untreated control of *H. pylori* (=100%). Positive control: 3'sialyllactose (15 mM).

| Test compound | Amino acid sequence | rel. adhesion in [%] (±SEM; n = 3) | |
|---|---|---|---|
| | | 75 µM | 150 µM |
| S3B | Ala-Phe-Asn-Val-Asn-Arg (SEQ ID NO: 8) | 97 ± 4 | 104 ± 1 |
| S3C | Leu-Glu-Asp-Ala-Phe-Asn-Val-Asn-Arg (SEQ ID NO: 9) | 95 ± 5 | 100 ± 4 |
| S3D | Asp-Ala-Phe-Asn-Val-Asn-Arg (SEQ ID NO: 10) | 89 ± 4 | 89 ± 3 |
| S3E | Asp-Phe-Leu-Glu-Asp-Ala-Phe-Asn-Val (SEQ ID NO: 11) | 91 ± 4 | 91 ± 4 |
| S3F | Asp-Phe-Leu-Glu-Asp-Ala-Phe (SEQ ID NO: 12) | 85 ± 3 | 90 ± 5 |
| S3G | Leu-Glu-Asp-Ala-Phe-Asn-Val (SEQ ID NO: 13) | 93 ± 2 | 94 ± 3 |
| S3H | Asp-Ala-Phe | 104 ± 6 | 105 ± 1 |
| untreated control | — | 100 ± 2 | 100 ± 2 |
| positive control | — | 70 ± 5 | 70 ± 5 |

A similar experiment was performed as described in the example of WO 2008/043424. Briefly, the pea protein digest was micro-fractionated by nano-reversed-phase chromatography (C18) and each fraction spotted online on a MALDI target. Each of the 832 spots was checked for the presence of the claimed peptides S3 (m/z 1339) and S5 (m/z 1418) by MALDI-TOF mass spec. In conclusion peptide S5 could not be identified at all. Peptide S3 has been found in trace amounts only.

1.4 In Situ Adhesion Inhibition of *H. pylori*

For confirmation of these results fraction F3, as well as peptide S3 were investigated on anti-adhesive activity in the in situ assay on human gastric tissue. In situ experiments with histological sections of human gastric mucosa and FITC-labelled *H. pylori* were performed according to Lengsfeld et al, 2004, J. Agricul. Food Chem: 52, 1495-1503, and evaluated by fluorescent microscopy. The adhesion of FITC-labelled *H. pylori* to the epithelium was assessed by fluorescent microscopy and imaging. The quantity of adhering bacteria to the epithelial surface was evaluated under double blinded conditions. Maximal adhesion was expressed as total 100% adhesion. The fluorescence area intensity was calculated by ImageJ® software (Olympus, Germany), standardizing the fluorescent area of the negative control as 100%.

*H. pylori*, pre-treated with fraction F3 (1.0 mg/ml) showed a strongly diminished adhesion in this test system (about 70% inhibition). Also S3 (300 µM) reduced the bacterial adhesion strongly (about 40% inhibition). These data clearly confirm the anti-adhesive activity of F3 and S3. On the other side the bioassay-guided fractionation indicated also a kind of non-linear activity profiling: the anti-adhesive effects were not steadily increasing during the peptide purification steps, but were getting less for the individual peptides isolated and tested. This is a clear indication for the presence of other active compounds in the mixture, influencing the anti-adhesive properties of the mixture in a synergistic way.

1.5 Structure-Activity Relations

For a structure activity relation of the active undecaptide S3 various fragments, differing in lengths were synthesized (S3A to S3H, see Tab. 1). Functional testing demonstrated a general loss of inhibitory strength compared to the native peptide S3. Only peptides S3D, E, F and G slightly blocked adhesion (about 10% reduction). If compared to S3 amino acids sequence a homologous motif with the terminal and integral tripeptide sequence, namely Asp-Ala-Phe, can be identified. Hence, the synthesized tripetide (Asp-Ala-Phe) S3H was tested and shown to be inactive, which possibly means that this sequence can only be functionalized, if integrated into a longer peptide chain. We assume that most probably the entire peptide sequence of at least 11 amino acids as found in S3 is necessary for its inhibitory activity to the bacterial adhesin, due to a possible formation of three-dimensional peptide folding, necessary for interactions with the receptor target.

The existence of certain secondary structure and three-dimensional peptide folding can change functionality of peptides. For that preliminary conformational modelling experiments, with the molecular operating environment (MOE) software, of the different peptides indicated a high degree of folding of the undecapeptide S3 which was clearly absent in the low-molecular peptide fragments S3A to S3H (data not shown).

1.6 Specificity of Adhesion Prevention

The specificity of the active peptides towards *H. pylori* outer membrane proteins (OMP) was shown by a dot blot glycoconjugate assay according to previously described methods [Walz, et al 2005, *Glycobiology*, 15, 700-708; Valkonen et al, 1994, 62 (9), 3640-3648.]

0.2 µm pore size polyvinylidene fluoride (PVDF) membranes were spotted with 2 µl of a solution, containing 1 µg of glycoproteins and neoglycoproteins.

A representative selection of typical ligands for *H. pylori* adhesins used for these experiments were Lewis[b] and H type I blood group antigen conjugates, interacting with the OMP BabA, 3'-sialyllactose interacting specifically with the OMP HpaA, sialyl-Lewis a and laminin known for interacting with the OMP SabA, and fibronectin with a not yet determined bacterial adhesin affinity. Further, human serum albumin (HSA) and bovine serum albumin (BSA) were used as controls to exclude non-specific binding of H. pylori to spotted compounds on the membrane. In addition 6'-sialyllactose was used to demonstrate the binding specificity of HpaA to 3'-sialyllactose. The fluorescence of adherent pre-treated and untreated labelled bacteria was measured.

In cases of pre-treatment of H. pylori with F3 a strong reduction of bacterial interaction with Lewis$^b$-, H type I-, and 3'-sialyllactose-HSA conjugates as well as with fibronectin was observed. F3 also affected in a smaller degree the binding to sialyl-Lewis$^a$ conjugate, but not to spotted laminin. These finding clearly indicate that F3 interacts specifically with H. pylori adhesins BabA, HpaA, fibronectin-binding adhesion and in less stronger way also with SabA In contrast peptides S3 and S5 exhibited only inhibition of Lewis$^b$-HSA mediated adhesion, suggesting inhibition of the BabA adhesin, while other adhesins were not significantly influenced.

In conclusion, these inhibitions suggest either a strong mimicry or additional binding sites of peptides from F3 to known receptor structures of BabA, HpaA, SabA and to a not yet identified adhesin with affinity to the ECM protein fibronectin. The purified peptides were significantly less active than the more complex fractions, which is due to the monovalent inhibition of a single bacterial adhesin by the purified peptide. In contrast, the use of a complex heterogenic mixture is able to interact with H. pylori OMPs in a multi-target strategy and therefore lead to a blocking of several proteins, responsible for the bacterial adhesion. This clearly demonstrates that in the scenario of different relevant OMPs for an adhesion process, complex mixtures can possibly be used much more effective than highly purified single compounds.

The present results of example 1 are indicative for the advantages to use pea protein hydrolysate and/or pea peptides for the treatment and/or prevention of H. pylori infections and/or a disease associated with infection by H. pylori in mammals.

---

The invention claimed is:

1. A composition comprising a lipid, protein and carbohydrate constituent, wherein the lipid constituent provides 5 to 50% of the total calories, the protein constituent provides 5 to 50% of the total calories and the carbohydrate constituent provides 15 to 90% of the total calories, wherein the protein constituent comprises:
   (i) at least one protein source consisting of pea protein hydrolysate, wherein the pea protein hydrolysate is obtained by hydrolysis with a protease in the absence of chymotrypsin and wherein the pea protein hydrolysate comprises over 35 wt % peptides with a size between 1 and 2.5 kDa based on total weight of the pea protein hydrolysate, and
   (ii) at least one nitrogen source selected from the group consisting of milk proteins, milk protein hydrolysate, egg proteins, egg protein hydrolysate, soy protein, soy protein hydrolysate, wheat protein, wheat protein hydrolysate, rice protein, rice protein hydrolysate, free amino acids and mixtures thereof.

2. The composition according to claim 1, comprising at least one selected from the group consisting of hydrolysed cow's whey, non-hydrolysed cow's whey, hydrolysed cow's casein, non-hydrolysed cow's casein, hydrolysed soy protein and non-hydrolysed soy protein.

3. The composition according to claim 1, comprising a soluble, non-digestible, fermentable oligosaccharide.

4. The composition according to claim 1, having an osmolality between 50 and 500 mOsm/kg.

5. The composition according to claim 1, in the form of a nutritional or pharmaceutical composition.

6. The composition according to claim 1, wherein the pea protein hydrolysate comprises a peptide selected from the group consisting of Xaan-Asp-Phe-Leu-Glu-Asp-Ala-Phe-Asn-Val-Asn-Arg-Xaam (SEQ ID NO: 14) and Xaan-Glu-Leu-Ala-Phe-Pro-Gly-Ser-Ala-Gln-Glu-Val-Asp-Arg-Xaam (SEQ ID NO: 15), wherein each Xaa independently can be any amino acid and n and m are integers independently ranging from 0-10.

7. A composition comprising a lipid, protein and carbohydrate constituent wherein the lipid constituent provides 5 to 50% of the total calories, the protein constituent provides 5 to 50% of the total calories and the carbohydrate constituent provides 15 to 90% of the total calories, wherein the protein constituent comprises:
   (i) at least one protein source consisting of peptides selected from the group consisting of Xaan-Asp-Phe-Leu-Glu-Asp-Ala-Phe-Asn-Val-Asn-Arg-Xaam (SEQ ID NO: 14) and Xaan-Glu-Leu-Ala-Phe-Pro-Gly-Ser-Ala-Gln-Glu-Val-Asp-Arg-Xaam (SEQ ID NO: 15), wherein each Xaa independently can be any amino acid and n and m are integers independently ranging from 0-10, and (ii) at least one nitrogen source selected from the group consisting of milk proteins, milk protein hydrolysate, egg proteins, egg protein hydrolysate, soy protein, soy protein hydrolysate, wheat protein, wheat protein hydrolysate, rice protein, rice protein hydrolysate, free amino acids and mixtures thereof.

8. A composition comprising a non-digestible oligosaccharide selected from the group consisting of trans-galactooligosaccharide, fructo-oligosaccharides, uronic acid oligosaccharide and sialyllactose and (a) pea protein hydrolysate, which is obtained by hydrolysis with protease other than chymotrypsin, wherein the pea protein hydrolysate comprises over 35 wt % peptides with a size between 1 and 2.5 kDa based on total weight of the pea protein hydrolysate; and/or (b) at least one peptide selected from the group consisting of Xaa$_n$-Asp-Phe-Leu-Glu-Asp-Ala-Phe-Asn-Val-Asn-Arg-Xaa$_m$ (SEQ ID NO: 14) and Xaa$_n$-Glu-Leu-Ala-Phe-Pro-Gly-Ser-Ala-Gln-Glu-Val-Asp-Arg-Xaa$_m$ (SEQ ID NO: 15), wherein each Xaa independently can be any amino acid and n and m are integers independently ranging from 0-10.

* * * * *

SEQUENCE LISTING

<160> NUMBER OF SEQ ID NOS: 15

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Isolated peptide from pea protein hydrolysate

<400> SEQUENCE: 1

Asp Phe Leu Glu Asp Ala Phe Asn Val Asn Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Isolated peptide from pea protein hydrolysate

<400> SEQUENCE: 2

Glu Leu Ala Phe Pro Gly Ser Ala Gln Glu Val Asp Arg
1               5                   10

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Isolated peptide from pea protein hydrolysate

<400> SEQUENCE: 3

Leu Asp Ala Leu Glu Pro Asp Asn Arg Ile Glu Ser Glu Gly Gly Leu
1               5                   10                  15

Ile Glu Thr Trp Asn Pro Asn Asn Lys
            20                  25

```
<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Isolated peptide from pea protein hydrolysate

<400> SEQUENCE: 4

Leu Asn Ile Gly Pro Ser Ser Ser Pro Asp Ile Tyr Asn Pro Glu Ala
1               5                   10                  15

Gly Arg

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Isolated peptide from pea protein hydrolysate

<400> SEQUENCE: 5

Trp Glu Arg Glu Glu Asp Glu Glu Gln Val Asp Glu Glu Trp Arg
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Isolated peptide from pea protein hydrolysate

<400> SEQUENCE: 6

Gly Asp Phe Glu Leu Val Gly Gln Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Phe Leu Glu Asp
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Phe Asn Val Asn Arg
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Glu Asp Ala Phe Asn Val Asn Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ala Phe Asn Val Asn Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Phe Leu Glu Asp Ala Phe Asn Val
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Phe Leu Glu Asp Ala Phe
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Glu Asp Ala Phe Asn Val
1               5

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(10)
<223> OTHER INFORMATION: Any amino acid and this region may encompass
      0-10 residues
<220> FEATURE:
<221> NAME/KEY: MOD_RES
<222> LOCATION: (22)..(31)
<223> OTHER INFORMATION: Any amino acid and this region may encompass
      0-10 residues

<400> SEQUENCE: 14

Xaa Xaa Xaa Xaa Xaa Xaa Xaa Xaa Xaa Xaa Asp Phe Leu Glu Asp Ala
1               5                   10                  15

Phe Asn Val Asn Arg Xaa Xaa Xaa Xaa Xaa Xaa Xaa Xaa Xaa
            20                  25                  30

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(10)
<223> OTHER INFORMATION: Any amino acid and this region may encompass
      0-10 residues
<220> FEATURE:
<221> NAME/KEY: MOD_RES
<222> LOCATION: (24)..(33)
<223> OTHER INFORMATION: Any amino acid and this region may encompass
      0-10 residues

<400> SEQUENCE: 15

Xaa Xaa Xaa Xaa Xaa Xaa Xaa Xaa Xaa Xaa Glu Leu Ala Phe Pro Gly
1               5                   10                  15

Ser Ala Gln Glu Val Asp Arg Xaa Xaa Xaa Xaa Xaa Xaa Xaa Xaa
            20                  25                  30

Xaa
```